United States Patent [19]

Semler et al.

[11] Patent Number: 4,770,820

[45] Date of Patent: Sep. 13, 1988

[54] PROCESS FOR THE PREPARATION OF CARBAMOYL CHLORIDES DERIVED FROM SECONDARY AMINES

[75] Inventors: Günther Semler, Kelkheim; Georg Schaeffer, Hofheim am Taunus, both of Fed. Rep. of Germany

[73] Assignee: Hoechst Aktiengesellschaft, Frankfurt am Main, Fed. Rep. of Germany

[21] Appl. No.: 851,952

[22] Filed: Apr. 14, 1986

[30] Foreign Application Priority Data

Apr. 16, 1985 [DE] Fed. Rep. of Germany ....... 3513599

[51] Int. Cl.$^4$ ............................................. C07C 125/03
[52] U.S. Cl. .................................................. 260/544 C
[58] Field of Search .................................... 260/544 C

[56] References Cited

U.S. PATENT DOCUMENTS

| | | | |
|---|---|---|---|
| 2,251,892 | 8/1941 | Orthner et al. | 260/544 C |
| 2,480,088 | 8/1949 | Slocombe et al. | 260/544 C |
| 3,870,707 | 3/1975 | Somlo | 260/544 C |

OTHER PUBLICATIONS

*CRC Handbook of Chemistry and Physics* 60th Ed. (1979-1980) CRC Press, Boca Raton, Florida, publ., pp. C-106 to 109.

Houben-Weyl, Methoden der Organ. Chemie, Bd. E4, "Kohlensäurederivate" (1932), pp. 45 and 47.

*Primary Examiner*—Paul J. Killos
*Attorney, Agent, or Firm*—Curtis, Morris & Safford

[57] ABSTRACT

Carbamoyl chlorides derived from secondary aliphatic amines having alkyl groups which are branched in the 1-position are prepared by passing phosgene at an elevated temperature into the corresponding, initially taken—if appropriate dissolved in an inert solvent—secondary aliphatic amines having alkyl groups which are branched in the 1-position.

The reaction products are intermediates in various specialized fields, particularly in the plant protection sector.

15 Claims, No Drawings

PROCESS FOR THE PREPARATION OF CARBAMOYL CHLORIDES DERIVED FROM SECONDARY AMINES

Carbamoyl chlorides derived from secondary amines are compounds of the formula

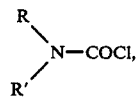

in which R and R' denote organic radicals.

In the main they are intermediates in various specialized fields, particularly in the plant protection sector.

The most frequently used method of preparing carbamoyl chlorides comprises reacting amines with phosgene; cf Houben-Weyl, Methoden der Organischen Chemie, Bd. E4 "Kohlensäure-Derivate" ("Methods of Organic Chemistry, Vol. E4 Carbonic Acid Derivatives") (1983) page 45. The reaction using secondary amines can be represented by the following equation—for example using dimethylamine as the starting amine:

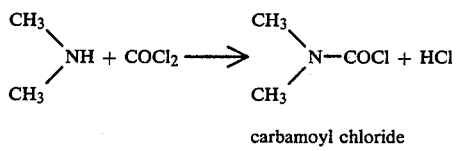

The carbamoyl chloride undergoes a further reaction with the starting amine very readily to give the corresponding urea derivative:

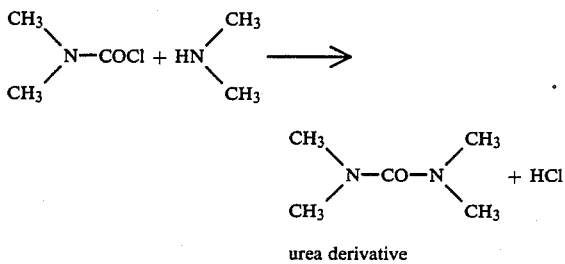

If it is desired to achieve high yields and a high state of purity of the carbamoyl chloride, it is therefore necessary to take steps to avoid the further reaction of the carbamoyl chloride to give the urea derivative.

For this reason it is recommended on page 47 of the Houben-Weyl volume mentioned above that, particularly for the preparation of carbamoyl chlorides of secondary amines, the phosgene should be introduced at a low temperature into a solution of the amine in an inert solvent. In this reaction, half of the amine is converted into the hydrochloride. The carbamoyl chloride can be isolated from this reaction mixture. It is more advantageous, however, to heat the mixture to over 100° C., while passing in further phosgene, whereupon the amine hydrochloride is converted into the carbamoyl chloride.

In connection with this it is admittedly then stated in this Houben-Weyl reference that it is frequently possible also to carry out the phosgenation immediately under hot conditions; however, concrete examples for the preparation of carbamoyl chlorides derived from secondary amines by passing phosgene into the initially taken amine at elevated temperatures are only described with secondary amines of a type in which the reactivity is considerably reduced by means of at least one aromatic radical. If this procedure is applied to purely aliphatic secondary amines such as, for example, N,N-di-n-propylamine or N,N-di-n-butylamine, the desired carbamoyl chloride is only obtained—as our own experiments have shown—in moderate purity and in yields between 60 and 80%, together with the urea derivatives formed by further reaction and the reaction products and secondary products of the latter with phosgene, as a result of the high reactivity of these amines. This results makes it seem scarcely suitable to apply the abovementioned method to the preparation of carbamoyl chlorides derived from secondary aliphatic amines, particularly on an industrial scale.

Surprisingly, it has now been found, however, that the method functions very well—i.e. yields of carbamoyl chlorides of, in some cases, considerably more than 90% of theory and with a high product purity—if secondary aliphatic amines in which the alkyl groups are branched in the 1-position are used as the starting materials.

The invention relates, therefore, to a process for the preparation of carbamoyl chlorides derived from secondary amines by passing phosgene under hot conditions into initially taken secondary amines—if appropriate amines dissolved in an inert solvent—which comprises using, as the secondary amines, secondary aliphatic amines having alkyl groups which are branched in the alpha- (or 1) position.

Preferred secondary aliphatic amines having alkyl groups which are branched in the alpha- (or 1) position are the compounds which fall under the formula I:

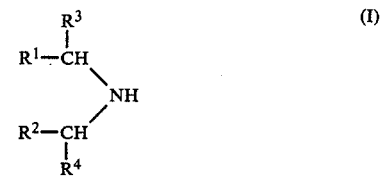

in which
$R^1$ and $R^2$ independently of one another denote $C_1$–$C_{20}$-alkyl, preferably $C_1$–$C_7$-alkyl,
$R^3$ and $R^4$ independently of one another denote $C_1$–$C_4$-alkyl, preferably $C_1$–$C_2$-alkyl,
or the groups $R^1+R^3$ and/or $R^2+R^4$ together denote $-(CH_2)_4-$ or $-(CH_2)_5-$.

Examples of starting amines falling under the formula I are N,N-diisopropylamine, N,N-di-secondary-butylamine, N,N-di-(2-methylbutyl)-amine, N,N-dicyclopentylamine, N,N-dicyclohexylamine and the like.

Particularly preferred starting amines are N,N-diisopropylamine, N,N-di-sec.-butylamine and N,N-dicyclohexylamine.

The starting amines can be dissolved in inert solvents which are customary in phosgenation reactions of this type, such as, for example, aromatic hydrocarbons (for example toluene, xylene and the like) and chlorinated hydrocarbons (chlorobenzene, dichlorobenzenes and the like). However, the use of solvents of this type is only necessary in cases where reaction mixtures become difficult to stir as a result of the intermediate formation of minimally soluble hydrochlorides.

Particularly in the event that N,N-di-sec.-butylamine is used as the starting amine, it is preferable to carry out the reaction without the use of an inert solvent.

In general, the reaction temperature is between about 80° and 160° C., preferably between about 100° and 130° C.

The preferred reaction pressure is normal pressure.

The process is carried out by passing phosgene into the secondary amine which has been initially taken—if appropriate dissolved in an inert solvent—and brought to the desired reaction temperature. Accurate metering of the phosgene is not necessary, nor is an excess of the latter. This makes it possible to avoid larger amounts of phosgene in the reaction mixtures, which is very important in view of the toxicity of this chemical.

The reaction mixture is worked up in a conventional manner, preferably by distillation.

Owing to the simple procedure, the yields of carbamoyl chlorides, which are in some cases consistently considerably over 90% of theory, and the high purity of the product, the process constitutes a considerable advance in this fields.

If starting amines of the formula I are employed, the carbamoyl chlorides obtained in accordance with the invention have formula II below:

$$\begin{array}{c} R^1-CH(R^3) \\ R^2-CH(R^4) \end{array}\!\!\!\!\!NH + COCl_2 \longrightarrow \begin{array}{c} R^1-CH(R^3) \\ R^2-CH(R^4) \end{array}\!\!\!\!\!N-COCl + HCl$$
(I)                                    (II)

$R^1$–$R^4$ have the meanings previously indicated in formula I.

The examples below are intended to illustrate the invention further. The invention examples (A) are followed by a few comparison examples (B) which show that the process according to the invention only functions in an unsatisfactory manner using secondary aliphatic amines which are not branched in the 1-position.

(A) INVENTIVE EXAMPLES

Example 1

N,N-Di-sec.-butylcarbamoyl chloride $$(CH_3-CH_2-\overset{\overset{\displaystyle CH_3}{|}}{CH})_2N-COCl$$

(by direct phosgenation of N,N-di-sec.-butylamine in the absence of solvent)

129.0 g (=1 mol) of di-sec.-butylamine were treated with phosgene gas at 110° C. until phosgene began to reflux on a reflux condenser operated at −20° C. The same temperature was then maintained for a further 2 hours. All told, in the course of approx. 5 hours about 190 g of phosgene were introduced, of which part escaped from the reaction vessel together with the hydrogen chloride formed during the reaction; the rest of the excess phosgene was then blown out by means of $N_2$ at 70° C. This left about 190 g (=99.2% of theory) of a crude product which was about 99% pure (GC) and which was purified by vacuum distillation. In the course of this, 182.0 g of a nearly colorless product passed over at 122° C./24 mbar and had a purity of 99.6%. The yield of 100% strength carbamoyl chloride was thus 181.3 g, corresponding to 94.7% of theory. A residue of 6.5 g (corresponding to 3.4% of the theoretical yield) remained in the distillation flask.

Example 2

N,N-Di-sec.-butylcarbamoyl chloride $$(CH_3-CH_2-\overset{\overset{\displaystyle CH_3}{|}}{CH})_2N-COCl$$

(by direct phosgenation of N,N-di-sec.-butylamine in chlorobenzene)

A mixture of 129.0 g of di-sec.-butylamine and 129.0 g of chlorobenzene was reacted with phosgene in accordance with Example 1. When the phosgenation was complete, the mixture was heated under reflux for a further hour, the residual phosgene was then removed by blowing out with nitrogen, and, after the solvent had been removed under a moderate vacuum, the main product was collected by distillation. N,N-di-sec.-butylcarbamoyl chloride was obtained in this manner in a yield of 186.0 g and in a purity of 99.8%. The yield of 100% strength carbamoyl chloride was 185.6 g, corresponding to 96.9% of theory. A residue of 2.5 g (corresponding to 1.2% of the theoretical yield) remained in the distillation flask.

Example 3

N,N-Diisopropylcarbamoyl chloride $$(CH_3-\overset{\overset{\displaystyle CH_3}{|}}{CH})_2N-COCl$$

(by direct phosgenation of N,N-diisopropylamine in chlorobenzene)

101.0 g (=1 mol) of diisopropylamine in 505.0 g of chlorobenzene were reacted with phosgene at 120° C. in accordance with Example 2, and the product was worked up. An approximately 99% strength reaction mixture (calculated without solvent) gave 154.5 g of an approximately 99% strength distillate boiling at 141° C./133 mbar and having a solidification point of 59° C. The yield of 100% strength carbamoyl chloride was thus 153.0 g, corresponding to 93.6% of theory.

Example 4

N,N-Dicyclohexylcarbamoyl chloride $$(\langle C_6H_{11}\rangle)_2 N-COCl$$

(by direct phosgenation of N,N-dicyclohexylamine)

45.3 g (=0.25 mol) of dicyclohexylamine were dissolved in 100 g of o-dichlorobenzene and treated with phosgene gas at 160° C. until no further absorption of phosgene could be observed. After a period of 2 hours at the same temperature to complete the reaction, the excess phosgene was blown out with $N_2$ at about 100° C., and the reaction mixture was distilled. Dicyclohexyl carbamoyl chloride distilled out at 135° C./1.2 mbar as a nearly colorless liquid, solidifying at 84° C. The yield was 57.8 g, corresponding to 94.9% of theory; the purity was virtually 100% (Cl titration).

A similar result was obtained when the phosgenation was carried out in 5 times the quantity of chlorobenzene at 110°–120° C.

(B) COMPARISON EXAMPLES

Comparison Example 1

N,N-Di-n-butylcarbamoyl chloride (CH$_3$—CH$_2$—CH$_2$—CH$_2$)$_2$N-COCl (by direct phosgenation of N,N-di-n-butylamine in chlorobenzene)

When di-n-butylamine was reacted with phosgene in accordance with (inventive) Example 2, a very thick reaction mixture which could scarcely still be stirred, was obtained soon after metering in phosgene had begun. The reaction mixture later became highly fluid once more and finally clear. After the amine had been completely reacted, the reaction mixture contained, in addition to the desired carbamoyl chloride, large amounts of N,N,N',N'-tetra-n-butyl urea (approx. 30%, calculated without the solvent) which reacted further with phosgene in a slow reaction, forming carbamoyl chlorides and decomposition products of itself. When a reaction product of this type, which contained a large amount of low-boilers and high-boilers in addition to approx. 70% of carbamoyl chloride (calculated without the solvent), was worked up by distillation, about 147 g of a product which was only approx. 86% pure were obtained. This corresponds to a yield of carbamoyl chloride of only 66.0% of theory.

Phosgenation without the use of a solvent in accordance with (inventive) Example 1 was virtually not possible, since the reaction mixture formed in this case could no longer be stirred.

Comparison Example 2

N,N-Diisobutylcarbamoyl chloride

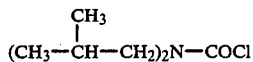

(by direct phosgenation of N,N-diisobutylamine in chlorobenzene)

Diisobutylamine was reacted with phosgene in accordance with (inventive) Example 2. The progress of the phosgenation was similar to that of di-n-butylamine in Comparison Example 1. Finally about 182 g of a product which was only 70% pure were obtained, corresponding to a yield of carbamoyl chloride of only 66.5% of theory.

Comparison Example 3

N,N-Di-n-propylcarbamoyl chloride (CH$_3$—CH$_2$—CH$_2$)$_2$N-COCl (by direct phosgenation of N,N-di-n-propylamine in chlorobenzene)

Di-n-propylamine was reacted with phosgene at 110° C. as in (inventive) Example 3. The reaction mixture formed was only about 67% pure (calculated without the solvent), and from this about 135 g of a product of approx. 80% purity were obtained by distillation. This corresponds to a carbamoyl chloride yield of only 66.1% of theory.

139 g of an approximately 95% strength distillate were obtained at a phosgenation temperature of initially 5° C. and later 80° C., the procedure being otherwise identical. This corresponds to a carbamoyl chloride yield of only 80.8% of theory.

What is claimed is:

1. A process for the preparation of a carbamoyl chloride derived from a secondary aliphatic amine which comprises passing phosgene into a solution of a secondary aliphatic amine having two alkyl groups which are branched in the 1-position in an inert solvent and kept at a temperature between about 80° and 160° C.

2. A process as claimed in claim 1, wherein the amine is of the formula I

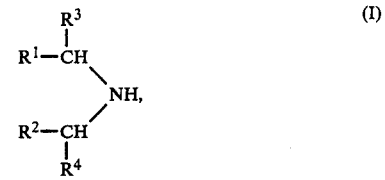

in which
R$^1$ and R$^2$ independently of one another are C$_1$–C$_{20}$-alkyl, and
R$^3$ and R$^4$ independently of one another are C$_1$–C$_4$-alkyl, or
the groups R$^1$+R$^3$ or R$^2$+R$^4$ or R$^1$+R$^3$ and R$^2$+R$^4$ together are —(CH$_2$)$_4$— —(CH$_2$)$_5$—.

3. A process as claimed in claim 2, wherein N,N-diisopropylamine, N,N-di-sec.-butylamine or N,N-dicyclohexylamine are used as secondary aliphatic amines having alkyl groups which are branched in the 1-position.

4. A process as claimed in claim 1, wherein the reaction is carried out at a temperature between about 100° and 130° C.

5. A process as claimed in claim 2, wherein in the amine of the formula I, R$^1$ and R$^2$ independently of one another are C$_1$–C$_7$-alkyl or wherein R$^3$ and R$^4$ independently of one another are C$_1$–C$_2$-alkyl.

6. A process for the preparation of di-sec.-butylcarbamoyl chloride which comprises passing phosgene into di-sec.-butylamine, the reaction system being kept liquid and at a temperature between about 80° and 160° C.

7. A process as claimed in claim 6, wherein the di-sec.-butylamine is kept at a temperature between about 100° and 130° C.

8. A process for the preparation of a carbamoyl chloride derived from a secondary aliphatic amine of the formula I,

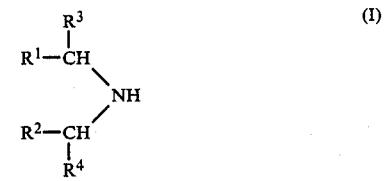

in which R$^1$ and R$^2$ independently of one another are C$_1$–C$_7$-alkyl and R$^3$ and R$^4$ independently of one another are C$_1$–C$_2$-alkyl, which comprises passing phosgene into a solution of an amine of the formula I in an inert solvent and being kept at a temperature between about 100° and 130° C.

9. A process as claimed in claim 8, wherein the amine is N,N-diisopropylamine.

10. A process as claimed in claim 8, wherein the amine is N,N-di-sec.-butylamine.

11. A process as claimed in claim 2, wherein the amine is N,N-dicyclohexylamine.

12. A process as claimed in claim 2, wherein in the amine formula I, $R^1$ and $R^2$ independently of one another are $C_1$–$C_7$-alkyl and wherein $R^3$ and $R^4$ independently of one another are $C_1$–$C_{12}$-alkyl.

13. In a process for the preparation of a carbamoyl chloride derived from a secondary aliphatic amine by reacting phosgene with a secondary aliphatic amine having two alkyl groups which are branched in the 1-position in an inert solvent at a temperature between about 80° and 160° C., the improvement which comprises passing phosgene into the solution of the secondary amine in the inert solvent.

14. In a process for the preparation of di-sec.-butyl-carbamoyl chloride by reacting phosgene with di-sec.-butylamine at a temperature between about 80° and 160° C., the improvement which comprises passing phosgene into di-sec.-butylamine in the liquid state.

15. In a process for the preparation of a carbamoyl chloride derived from a secondary aliphatic amine of the formula I,

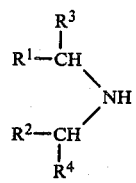

in which $R^1$ and $R^2$ independently of one another are $C_1$–$C_7$-alkyl and $R^3$ and $R^4$ independently of one another are $C_1$–$C_2$-alkyl by reacting phosgene with an amine of the formula I in an inert solvent at a temperature between about 100° and 130° C., the improvement which comprises passing phosgene into a solution of said amine in the inert solvent.

* * * * *

UNITED STATES PATENT AND TRADEMARK OFFICE
CERTIFICATE OF CORRECTION

PATENT NO. : 4,770,820
DATED : September 13, 1988
INVENTOR(S) : Semler et al.

It is certified that error appears in the above-identified patent and that said Letters Patent is hereby corrected as shown below:

Column 7, line 10 (Claim 12, line 2), after "amine" insert --of the--;

Column 7, line 12 (Claim 12, line 4), change "$C_1$-$C_{12}$-alkyl" to --$C_1$-$C_2$-alkyl--.

Signed and Sealed this

Fourteenth Day of March, 1989

Attest:

DONALD J. QUIGG

Attesting Officer

Commissioner of Patents and Trademarks